United States Patent [19]
Selby et al.

[11] Patent Number: 5,922,973
[45] Date of Patent: Jul. 13, 1999

[54] NOACK-TYPE TEST UNIT

[75] Inventors: Theodore W. Selby; Richard H. Hall, both of Midland; Joseph S. Trombley, Auburn; James R. Cotter, Bay City; Marc J. Hildebrandt, Midland, all of Mich.

[73] Assignee: Tannas Co., Midland, Mich.

[21] Appl. No.: 08/893,632

[22] Filed: Jul. 11, 1997

Related U.S. Application Data

[63] Continuation-in-part of application No. 08/773,342, Dec. 26, 1996, abandoned.

[51] Int. Cl.$^6$ .............................. G01N 1/00; G01N 25/56; A47B 81/00
[52] U.S. Cl. ............................... 73/864; 312/209; 374/54
[58] Field of Search .................. 312/209, 138.1, 312/139, 139.1, 237, 319.1, 319.2, 319.3, 319.4, 326, 329, 352; 269/296, 299; 211/59.3; 248/313; 73/864; 374/54

[56] References Cited

U.S. PATENT DOCUMENTS

| | | | |
|---|---|---|---|
| 1,120,050 | 12/1914 | Goggin | 312/319.1 X |
| 1,526,062 | 2/1925 | Golden | 312/237 X |
| 2,116,442 | 5/1938 | McCluer | 422/101 X |
| 2,604,996 | 7/1952 | Smith | 211/59.3 |
| 2,667,397 | 1/1954 | Hallisey | 312/209 X |
| 2,901,586 | 8/1959 | Krusik | 312/209 X |
| 3,284,148 | 11/1966 | Ramniceanu | 312/209 |
| 3,484,077 | 12/1969 | Porter | 422/103 X |
| 3,490,736 | 1/1970 | Snyder | 422/103 X |
| 3,525,593 | 8/1970 | Thompson | 312/209 X |
| 3,584,927 | 6/1971 | Ott et al. | 312/209 X |
| 3,603,550 | 9/1971 | Byrd | 248/313 |
| 3,874,754 | 4/1975 | Saunders et al. | 312/209 |
| 4,002,382 | 1/1977 | Wolf et al. | 312/209 |
| 4,259,293 | 3/1981 | Najarian et al. | 422/109 |
| 4,506,775 | 3/1985 | LeBron et al. | 194/249 |
| 4,559,879 | 12/1985 | Hausser | 108/136 |
| 4,689,237 | 8/1987 | Fabre | 426/521 |
| 4,733,842 | 3/1988 | Wilkerson | 248/231.51 |
| 4,784,360 | 11/1988 | Mok | 248/313 |
| 4,828,119 | 5/1989 | Pingleton | 211/59.3 |
| 4,962,799 | 10/1990 | Ming-Tang | 269/296 X |
| 5,181,620 | 1/1993 | Watt | 211/59.3 |
| 5,341,542 | 8/1994 | Hannan et al. | 312/319.4 X |
| 5,667,302 | 9/1997 | Selby et al. | 374/54 |
| 5,692,832 | 12/1997 | Selby | 374/54 |

OTHER PUBLICATIONS

08/425588, Selby et al., Apr. 20, 1995.
Selby et al., "Engine Oil Volatility Studies—Generation of Phosphorus", 1995.

*Primary Examiner*—Harshad Patel
*Assistant Examiner*—Robin C. Clark
*Attorney, Agent, or Firm*—Christopher John Rudy

[57] ABSTRACT

Apparatus for sample volatilization and collection has a housing which includes volatilization and collection equipment mounting adaptation(s) and a pressure gage for monitoring internal pressure of such equipment. The housing can contain power and/or power line(s) to include for heating the equipment and/or providing a vacuum for the equipment, and/or a device for providing an internal vacuum for the equipment; additional condition monitoring gage(s), and so forth. The apparatus can include the equipment, which can be especially adapted for Noack-type testing.

20 Claims, 4 Drawing Sheets

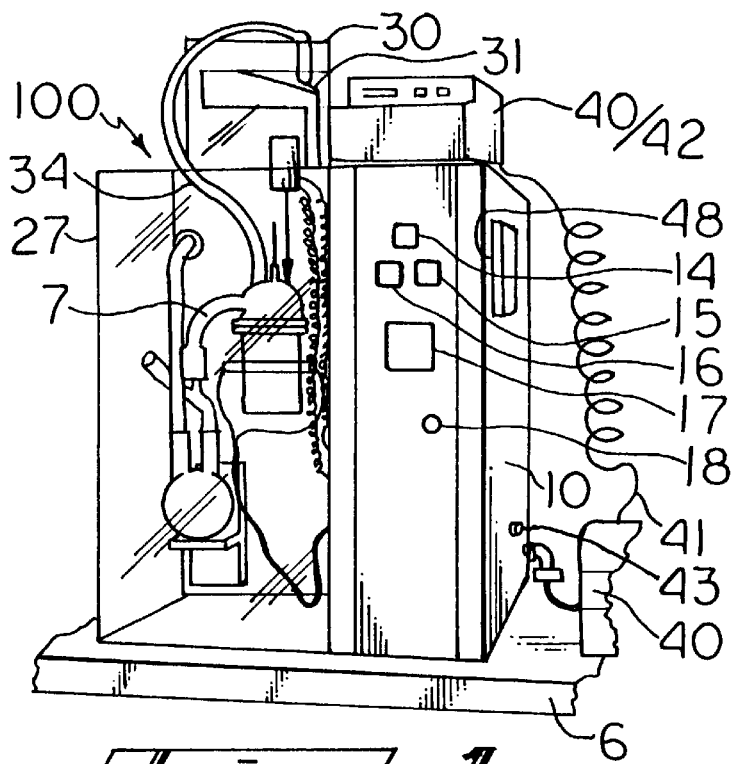
Fig. 1
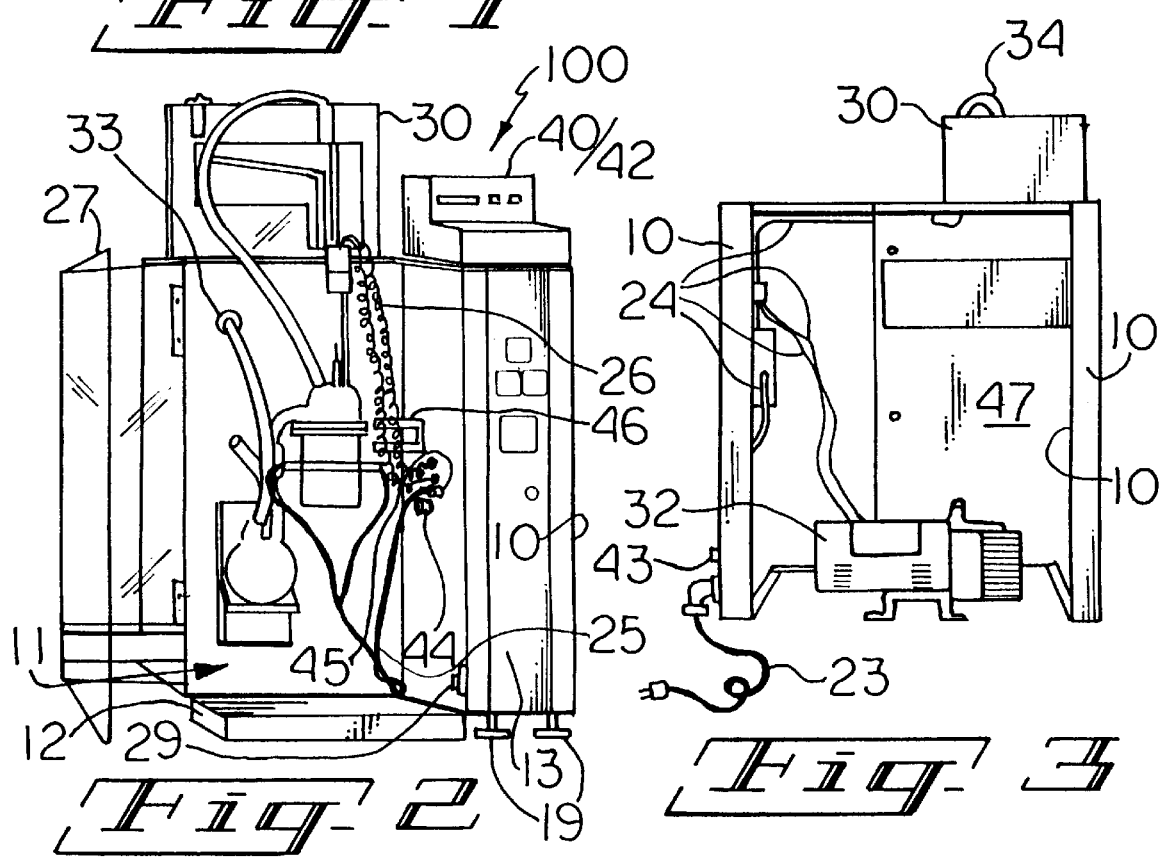
Fig. 2
Fig. 3

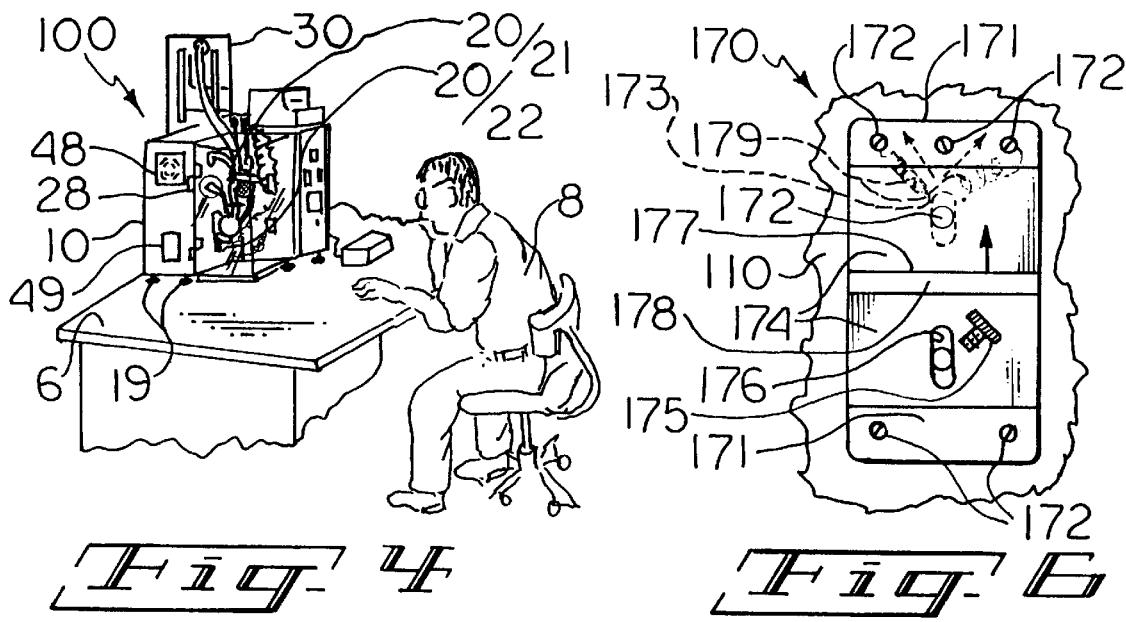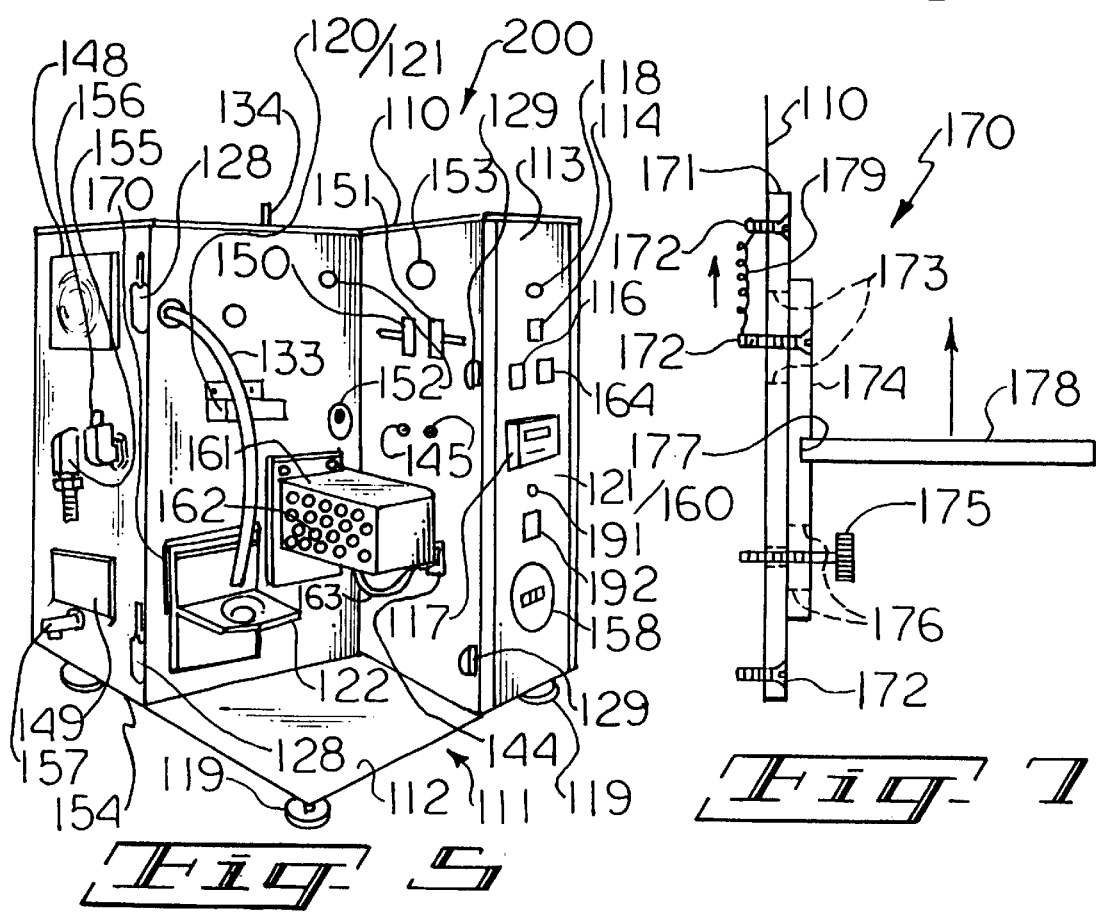

NOACK-TYPE TEST UNIT

This is a continuation-in-part of application Ser. No. 08/773,342, filed Dec. 26, 1996, now abandoned.

FIELD

This invention concerns test apparatus, and methods of making and using the same, useful in volatilization testing.

BACKGROUND

In U.S. patent application Nos. 08/425,588; 08/517,429 and 08/577,964—filed on Apr. 20, 1995; Aug. 21, 1995 and Dec. 26, 1995, respectively—are disclosed a fluid coalescing method and apparatus; vapor removal, and selective volatilization and collection. In the specification disclosures thereof, each of which is entirely incorporated herein by reference, are described, by means of general summation, the following:

Selby & Stephenson, '588: A method to coalesce matter comprises providing a suitable, narrow passageway for throughput of matter in a vapor state, and passing the matter in a vapor state through said passageway, under conditions such that the matter is coalesced into a more ordered state. An apparatus useful for coalescing of matter comprises a hollow housing in communication with at least one of—(A) a plurality of suitably narrow hollow passageways, and (B) a suitably narrow, elongately hollow, matter-coalescing passageways—for throughput of matter to include as a vapor therein.

Selby, '429: An apparatus useful for removal of vapor comprises—(A) a hollow housing capable of holding a solid or liquid sample and being subject internally to a vacuum; (B) a hollow, carrier-gas wand in the housing having a carrier-gas entry port in communication with a carrier-gas system external to the housing, and a carrier-gas exit port disposed internally in the housing and at a position proximate the sample such that entering carrier-gas can sweep across a surface of the sample or through a section of vapor from the surface of the sample which is near thereto, but generally would not macroscopically significantly disturb the surface of the sample if a liquid; and (C) an exit port in the housing for egress of carrier-gas/vapor from inside the housing. Consequently, in general, vapors, as obtained by evaporation or sublimation, can be removed from such a vessel by a sweeping of the carrier gas gently above and/or across the surface of the sample and upward to the exit port. Methods of vapor retrieval and use of the apparatus are also provided thereby.

Selby & Cluff, '964: A method for selective volatilization and collection of a substance comprises providing a substance in a coalesced state, the substance having a surface boundary in contact with matter provided in the gaseous state, said provided substance and matter being substantially contained in a system for at least a portion of time the same are provided; providing thermal energy to the system including to the substance, and providing a current within the matter in the gaseous state, the current having an origin external to the system, such that, substantially without boiling being observable by the naked eye and without substantially disturbing the surface boundary of the substance, at lease one component of the substance becomes volatilized and crossed the surface boundary into the matter provided in the gaseous state; gently sweeping the volatilized substance component(s) in the matter in the gaseous state away from the boundary of remaining substance and the matter; and collecting the volatilized substance component(s). An apparatus useful with the method can comprise a generally enclosed vessel capable of holding the substance, a gaseous matter entry port such that its exit end, for providing the gaseous matter to the interior of the vessel, is disposed above the boundary of the substance, and an exit/collection port with means for collection of the volatilized component(s) of the substance. An entry port wand with a throttle and/or porous ball or director channel(s), or other means of tempering and/or directing the incoming gaseous matter, may be provided with the apparatus.

By the foregoing, analyses, especially of oil samples, are improved, and vapor collection efficiency is high. And yet, operation of the aforementioned apparatus in analytical testing may be somewhat if not significantly cumbersome.

Accordingly, improvement thereover is desired.

SUMMARY

The present invention provides an apparatus for sample volatilization and collection comprising a housing which includes volatilization and collection equipment mounting adaptation(s) and a pressure gage for monitoring internal pressure of said equipment. The housing can contain power and/or power line(s) to include for heating said equipment and/or providing a vacuum therefor, and/or a device for providing an internal vacuum for said equipment; additional condition monitoring gage(s), and so forth. The apparatus can include said equipment, which can embrace that disclosed in the specifications of the aforementioned Selby et al., '588; Selby, '429, and Selby et al., '964, patent applications; in the present specification, and so forth. Methods to make and use the apparatus are provided.

The invention is useful in analyses.

Notably, by the invention, volatilization and collection testing is significantly advanced. Apparatus is made more dependable and much easier to use, with ergonomic placement of components of the apparatus a preferred feature hereof. Thus, Noack-type testing and the advancements thereto, for example, for testing oil samples, are greatly facilitated.

Numerous further advantages attend the invention.

DRAWINGS IN BRIEF

The drawings form part of the specification hereof. As concerns the same, the following is briefly noted:

FIG. 1 is a right front elevational view of an apparatus of the invention.

FIG. 2 is a left front elevational view of the apparatus of FIG. 1, with its see-through, front shield opened.

FIG. 3 is a rear view of the apparatus of FIGS. 1 & 2, with its rear panel cover removed.

FIG. 4 is a another left elevational view of the apparatus of FIGS. 1–3, with an operator present.

FIG. 5 is left front elevational view of another embodiment of the apparatus of the invention, in a stage of partial assembly but nearing completion.

FIG. 6 is a front plan view of a lift bracket found in the apparatus of FIG. 5.

FIG. 7 is a side plan view of the lift bracket of FIG. 6.

DETAILED DESCRIPTION

Figure 8:
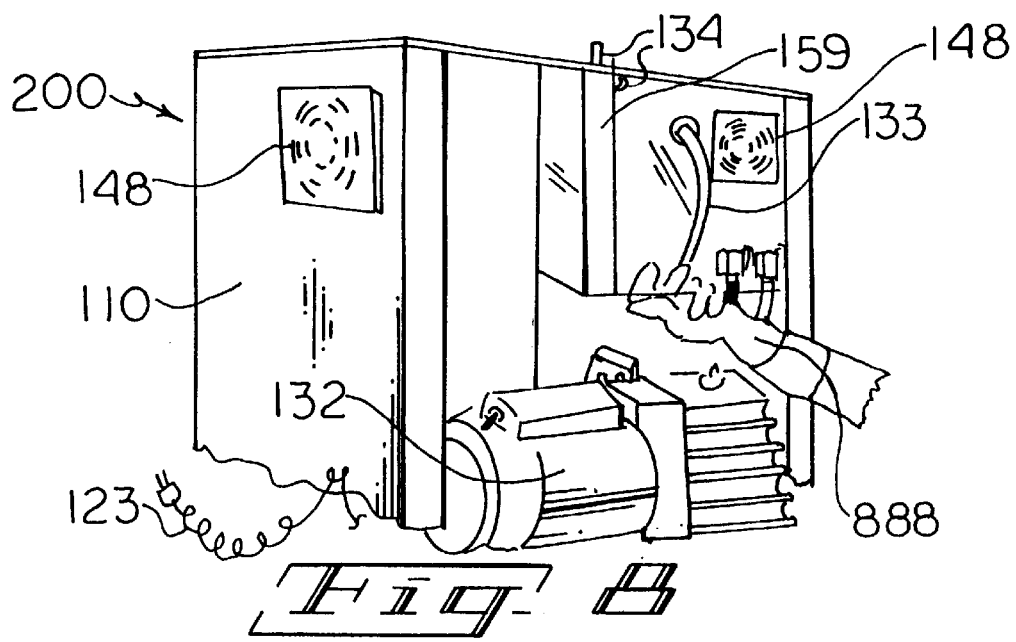
FIG. 8 is a rear view of the apparatus of FIG. 5, with its rear panel cover removed and a shock cover being fitted.

The invention can be further understood by reference to the present detail, which may be taken in conjunction with the referenced drawings and descriptions. The same is to be taken in an illustrative and not necessarily limiting sense.

In reference to the drawings, in FIGS. 1–4 is depicted apparatus 100 for volatilization and collection; the same is adapted for set-up and operation on benchtop 6 by operator 8 and has housing 10, which can be of any suitable material as of steel on which is volatilization and collection equipment mounting adaptation(s) 20 of suitable material, e.g., of plastic and/or stainless steel, to mount volatilization and collection equipment 7, and a pressure gage panel 30, e.g., of a see-through plastic, to mount a pressure gage device, e.g., manometer 31, such as is disclosed by U.S. Pat. No. 1,917,637 which is incorporated herein by reference, for monitoring internal pressure of the equipment 7. The adaptation(s) 20 can include volatilization chamber mount 21 and collection chamber mount 22, which can be mounted onto a rear wall of the housing 10 in recessed, work volume 11 of the apparatus 100. As or in addition to that disclosed hereby, the equipment 7 can be that disclosed in the specifications of the aforementioned Selby et al., '588; Selby, '429, and Selby et al., '964, applications, and so forth and the like. Bottom tray 12 of stainless steel, or of another suitable material, can be present and/or attached to the housing 10 so as to provide a basin or shield to catch and protect benchtop 6 from spills. Phenolic plastic front panel 13 may be present and attached to the housing 10, which panel 13 when removed may provide access to an automatic transformer, for example, toward the bottom of the inside behind the panel 13, and to wiring, switch, and control connections, for example, toward the top of the inside behind the panel 13, and so forth, and have mounted thereon such devices as main power on/off switch 14, equipment 7 heating mantle power on/off switch 15, vacuum pump on/off switch 16, temperature monitoring readout panel 17, over-heating warning light 18, and so forth, which are connected to appropriate power lines and/or are in communication with the appropriate operating parts such as by wire, radio, hollow conduit, and so forth. Feet 19 support and level the apparatus 100. As shown, the apparatus 100 contains a power source line 23 and power distribution lines 24 to include power line 25 for heating the mantle of the equipment 7 and relay line 26 for monitoring temperature(s) inside the equipment 7 during calibration and/or operation as sensed by a thermocouple. The operator 8 may be shielded from the equipment 7 by see-through, front shield 27, e.g., of polycarbonate plastic, when the same is closed (FIGS. 1 & 4). The shield 27 may be mounted on hinge(s) 28 so as to swing it open (FIG. 2) to order to provide access to the work volume 11 for set-up and cleaning of the unit. Latch 29 can stop and/or secure the shield 7. Vacuum-providing motor 32 may be mounted inside the housing 10 and provide a vacuum for the equipment 7 through connection/line 33 with other lines such as line 34 in connection with the manometer 31 also present with the apparatus 100. Other features may be present to include those which can be for communication with auxiliary equipment 40, e.g., line 41 can relay power and/or information to output printer 42. Auxiliary jack socket 43 may be provided for connections for additional equipment. Permanent jack sockets other electric or mechanical fixtures may be mounted on the housing, e.g., as seen in FIG. 2, in the work volume 11 may be general power jack 44, heating mantle power supply jack 45, thermocouple jack 46. Inside panel 47 may be provided so as to provide support for mounted components. Openings 48 for cooling fans and/or access thereto may be provided in the housing 10. Window 49 may be provided, for example, for viewing the oil level in the vacuum pump 32.

The apparatus hereof can be made by standard fabrication methods or methods analogous thereto. The methods are those suited for the materials employed and design desired, as any person skilled in the art would appreciate.

The apparatus hereof can be employed in volatilization and collection analyses and/or processing. For an example of the former, the apparatus may be employed in Noack-type testing according to appropriate test methodology such as along the lines of a standard Noack test, Japanese Standard JPI-55-41-93 or European Standard CEC L-40-T-87, or of an improved test method as disclosed in the aforementioned, incorporated-by-reference patent applications. Such improved testing may be referred to as Selby-Noack liquid sample testing, for example, for engine oil samples. For an example of the latter, cuts of a liquid sample, say, an oleaginous sample, may be volatilized and select fraction(s) collected with high efficiency and at high purity.

In Selby-Noack liquid sample testing, for example, of engine oil at some two hundred fifty degrees C., employing the glassware and associated equipment embraced by that disclosed in the specifications of the aforementioned Selby et al., '588; Selby, '429, and Selby et al., '964, patent applications; and in the present specification, the number of molecules in the volatilization chamber of the vessel is tightly controlled with a low, not high or hard, vacuum, and with the orifice and/or throttle, etc., delivered to the chamber through a wand or equivalent. Low vacuum and gentle sweeping with the carrier gas such as air permits molecules to leave the sample surface as a vapor at certain, controlled, relatively low energy values, versus the normal effect of a hard vacuum without such herding. It appears that the swept molecules do not impart much heat to the walls of the vessel since no distillation/condensation line is observed in Selby-Noack testing versus that seen in common set-ups and testing. Perhaps energy is imparted or contained within the matter gently swept with the carrier gas stream. Thus, the degrees of freedom of the swept vapor molecules seem to be reduced by the select removal of sample in such a "non-energetic" manner, and so, the testing has significant accuracy and precision. The same effect may increase ease of coalescence.

Figure 9:
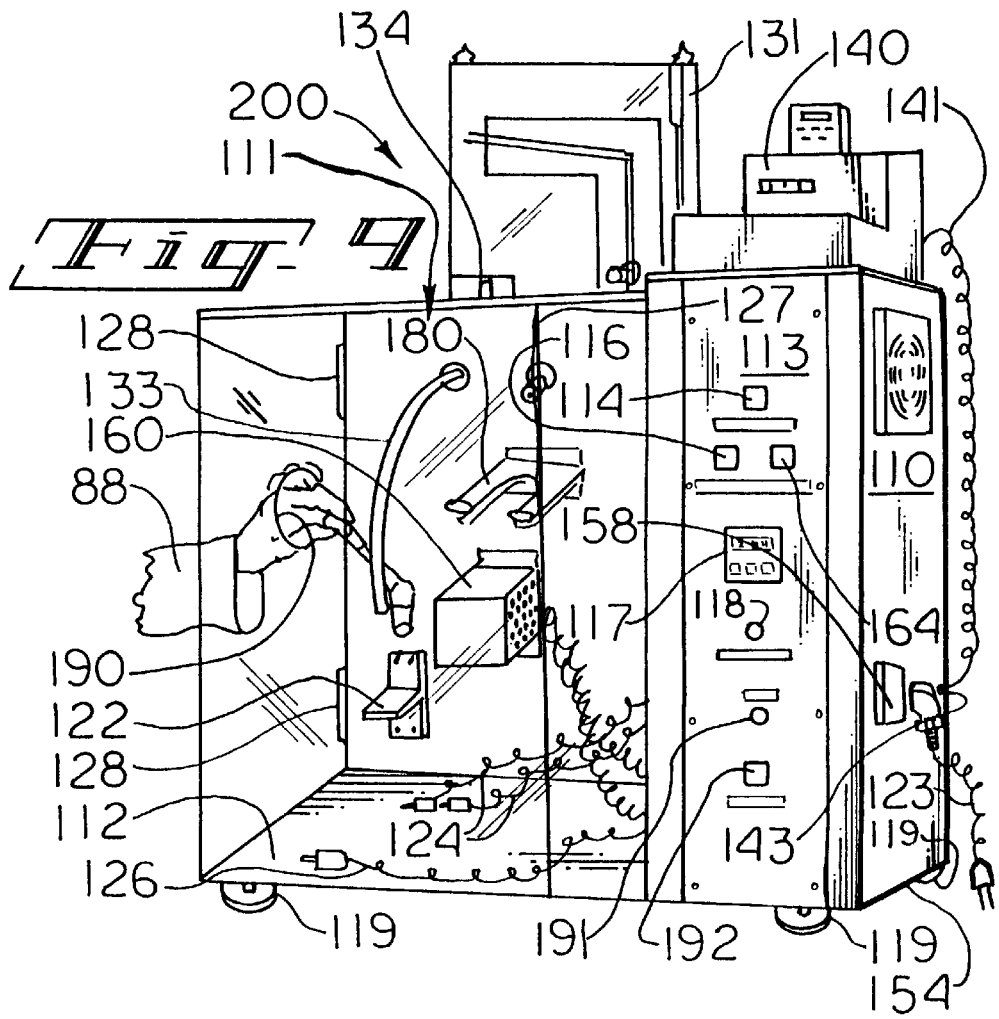
FIG. 9 is a right front elevational view of another embodiment of the apparatus of the invention, assembled but with most glassware removed save a coalescer being held to demonstrate a volatilization and collection equipment access opening.

In further reference to the drawings, in FIGS. 5–11 are depicted apparatus 200 and auxiliary equipment for use therewith. As with the apparatus 100, the apparatus 200 is adapted for set-up and operation of the so-called Selby-Noack Test testing, a modified Noack test, on a benchtop by an operator. The apparatus 200 includes similar components as the apparatus 100, as can be seen in FIGS. 5, 8, 9, as follows: housing 110; work volume 111; bottom surface or tray 112; front panel 113; main switch 114; vacuum pump switch 116; temperature monitoring readout controller panel 117; over-temperature warning light 118; feet 119; power source line 123; power distribution lines (not illustrated) and heating mantle power lines lines 124; relay line 126 for monitoring temperature inside the glassware test equipment; hinges 128, for example, of the bullet-shaped post type for easy removal and reinstallation of a front shield having complementary hinge holes; latch 129, for example, of the magnetic type; vacuum pump 132; vacuum line 133; auxiliary equipment 140, including line 141 for information to output printer 142; auxiliary jack socket 143; magnetic stirrer motor power jack 144, which may be used alternatively to power other auxiliary equipment; heating mantle power supply jack 145; cooling fan openings 148, the fans themselves of the exhaust type; window 149 for observing oil levels in the vacuum-providing motor 132.

Figure 10:
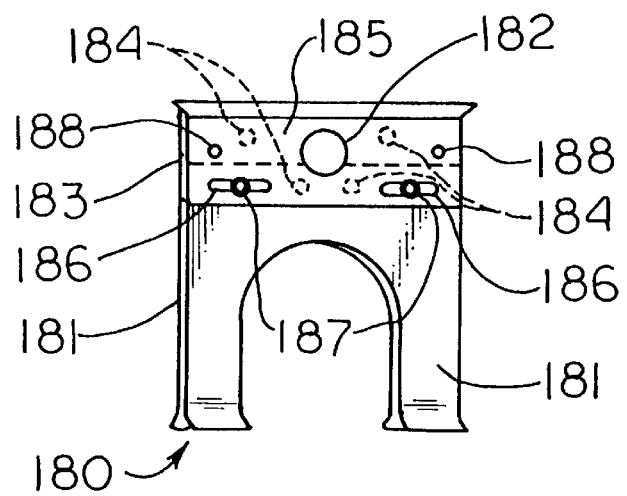
FIG. 10 is a top plan view of a volatilization chamber clamp.
Figure 11:
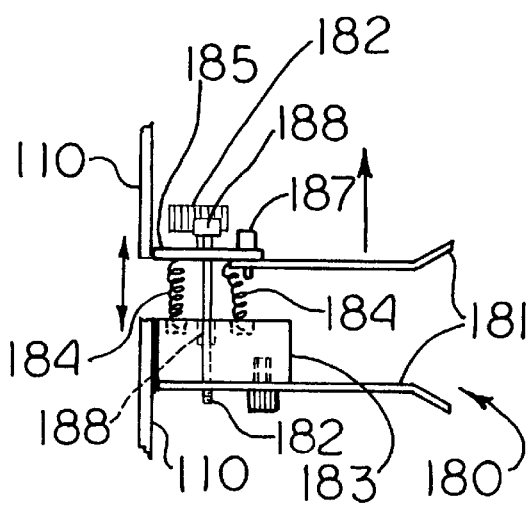
FIG. 11 is a side plan view of the clamp of FIG. 10.
Figure 12:
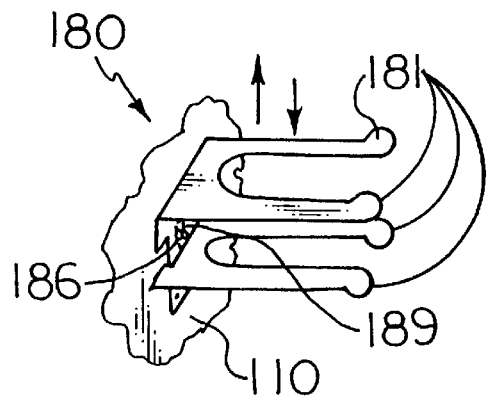
FIG. 12 is a perspective view of another embodiment of a volatilization chamber clamp.

In addition, heating mantle control is provided automatically through employment of the main power switch 114; control of high temperature shut off is provided through two sets of plugs 150, 151, through which thermocouple connections are made, the set 150 leading to the overheating monitor light 118 controlled by a suitable device such as a WATLOW model-92 device which shuts off power to the volatilization vessel heater and illuminates the light 118, and the set 151 leading to a temperature control circuitry device inside the housing cabinet 110 such as a WATLOW model-965A temperature controller in conjunction with a phase angle fired power control set to turn off power to the heating device when the thermocouple reaches a predetermined reading, for example, a 260-degree-C reading; auxiliary access holes 152 may be provided in the housing 110, and a cap 153, for example, of stainless steel in a match of the material of the vertical walls of the recessed work volume 111, may plug up such an access hole when not in use; base 154, for example, of carbon steel, which may be painted, underlies and supports the housing, and the bottom tray 112 may fold around the edges of the base 154. Volatilization and collection equipment mounting adaptations 120 include volatilization chamber mount 121, which may include not only magnetic stirring motor containing base 160, to include top 161, perforate sides 162, power supply cord 163 leading to the power jack 144, and lift bracket mount 170 (FIGS. 5–7), but also volatilization chamber clamp 180 (FIGS. 10–12). In a typical arrangement, however, holding force for the mount 121 to hold the volatilization chamber vessel is provided primarily through the clamp 180 with the lift bracket mount base 160/170 being raised up to the bottom of the vessel after it is clamped by the clamp 180. The magnetic stirring motor (not illustrated) may be activated by switch 164. Collection chamber mount 122 can be non-biasedly adjustable, for example, upwardly or downwardly with tightening knobs to secure the mount at the desired position, or, alternatively, be provided in the form of the upwardly-biased lift bracket mount 170, and have an optional, open-holed felt-lined flask pad on its base, the base, for example, of a plastic such as a paper-based phenolic plastic composite, e.g., well-known grade-XX, or have a resilient, cushioning elastomer pad, e.g., of Buna-N or silicone rubber, foamed or unfoamed, covering a simple, imperforate base, for example, of the phenolic, to cushion the bottom of a mounted collection flask. See-through front shield 127 (FIG. 9) generally of a suitable high-strength, transparent, solvent-resistant plastic such as an acrylic or polycarbonate plastic has volatilization and collection equipment access opening 190 in a side pane thereof, through which an operator 88 can adjust equipment such as a vapor coalescing valve when the shield 127 is in a closed position. Light 191 is for indicating heating in progress, and switch 192 is for activating power to heat the volatilization vessel (FIGS. 5 & 9). Other physical processing lines such as vacuum readout connection line 134, for example, can be internalized, at least in part, for use with the (U.S. Pat. No. 1,917,637) manometer 131. Although shown on a side of the housing 110 (FIG. 5), the following components may be more unobtrusively mounted on the rear of the cabinet housing 110: vacuum pump exhaust port 155, to which a conduit may be mounted so as to deliver the exhaust into the sphere of influence of a laboratory exhaust hood; oil filling plug 156 for access to the vacuum pump 132 s0 as to be able to fill the same with oil; and vacuum pump oil drain 157. Monitoring device 158 for monitoring the operating time of the vacuum pump 132 can be mounted on a front of the housing 110 (FIG. 5) or, preferably, on a side of the housing (FIG. 9). Shock cover 159, shown being fitted by assemblyman 888 (FIG. 8), can help shield persons from shock from electrical components when the rear cover (not illustrated) is removed. Power can be supplied through an AC power controller, for example, a 4- to 20-milliampere type. In Selby-Noack testing, as taught in the '588 application, a pressure differential in the same range as provided by the vacuum pump 132 may be provided by a pressured gas such as air and/or nitrogen without use of a vacuum pump.

It can be appreciated that, with the provision of the magnetic stirring motor containing base 160, the volatilization and collection equipment may have added in its volatilization vessel a magnetic stirring bar, and testing otherwise run without stirring can be run with stirring. It has been pleasantly found that such test methods, otherwise similar to those disclosed in the specifications of the aforementioned Selby et al., '588; Selby, '429; and Selby et al., '964, applications, are themselves efficient and reproducible in their own fashion. Accordingly, in a Selby-Noack test procedure, liquid in the volatilization vessel can be stirred at a stable, steady rate in order to accomplish this. For example, the stirring can be at about a 300-rotations-per-minute rate, done with a suitable magnetic stirring bar, e.g., a one-inch magnetic stirring bar, activated by the magnetic stirrer.

Overall, with respect to the apparatus 100 & 200, dimensions are any which are suitable for the purposes intended. For an example, dimensions can include those which follow, and these may be considered to be approximate: 24½-inch height, 26-inch height including feet 19/119; 19¼-inch rear width; 8-inch front instrument panel width; 16-inch long, e.g., right, side depth; 8-inch short, e.g., left, side depth.

In particular reference to FIGS. 6 & 7, the lift bracket 170, which, for example, is upwardly-biased in the direction of the arrows illustrated in these figures, can include base plate 171, which can be mounted to a wall of the housing 110 by fasteners such as screws 172, and which can contain elongate slot 173; slidable plate 174, which can be attached to the base plate 171 through a screw 172 that passes into and through the base plate slot 173 and through a settable device, for example, set screw knob 175 that can pass through slidable plate elongate slot 176 and be threaded into the base plate 171, and which plate 174 may contain a shelf-accommodating groove 177; shelf 178; and tensioning device 179. For example, the tensioning device 179 can be a spring or a set of two springs spanning screws 172 mounted to the base plate 171 and the slidable plate 174. Rubber bands and so forth may be employed as the tensioning device 179. The bracket 170 may be mounted to a wall of the housing 110 by standard devices, to include by fasteners such as screws, rivets, and clamps, and/or by gluing and so forth.

In reference to FIGS. 10–12, the clamp 180 may take the form of a member having two generally U-shaped tines 181. As shown in FIGS. 10 & 11, the tines 181 can be connected by one or more fasteners such as one or more screws 182 with a spacing block 183 between the tines 181. The clamp 180 may be explosively-biased such as through provision of a set of springs 184 of the compression type, for example, by four compression springs, mounted between the tines 181 into countersunk holes in the spacing block 183 and in upper tine support member 185. The member 185 may contain laterally disposed slots 186 through which short screws 187 may pass to be mounted in one of the tines 181 designated as the upper tine, thereby permitting lateral adjustment of the upper tine of the clamp for easier fitting of a two-part volatilization flask component for efficient testing. A set of glide posts 188, which may be screwed into the block 183, are provided to steady and secure the device 180. The tines 181 may have outwardly directed tips, generally with a set of tips (upper tine) directed up and the other set down. As shown in FIG. 12, the tines 181 are again generally U-shaped, but the upper tine is of a spring steel, for example, of stainless or carbon steel, and the lower tine is of a more rigid steel. The upper tine can be adjusted upward and downward such as by provision of vertical slots 189 (one depicted) in a vertical back part of the upper tine, which can be secured in place at the desired position of adjustment by short screws 186 (one depicted) of any suitable variety, including the wing nut type. In general, it should be appreciated that a clamp such as the clamp 180 is particularly useful when the two-art volatilization vessel has rounded glass sealing surfaces such as found with a domed or convexo-concavo mating configuration, as disclosed by Mr. Selby in the specification of the aforementioned '429 application. The rounded configuration can be otherwise difficult to seal completely while keeping ease of emplacement and removal of the clamp foremost in mind.

CONCLUSION

The present invention is thus provided. Numerous modifications can be effected within its spirit, the literal claim scope of which is particularly pointed out as follows:

We claim:

1. An apparatus for sample volatilization and collection comprising a housing, which includes at least one suitable equipment mounting adaptation, and a pressure gage for monitoring internal pressure of said equipment, wherein the housing is a three-dimensional structure having a recessed work volume having at least one vertical wall surface, and wherein the recessed work volume is such that it is physically accessible by an operator of the apparatus during volatilization and collection operation of the same.

2. The apparatus of claim 1, wherein the housing contains lines for power for heating said equipment and for providing a vacuum therefor, and a device for providing an internal vacuum for said equipment; at least one condition monitoring device additional to the pressure gage; the at least one suitable equipment mounting adaptation includes at least one volatilization and collection equipment mounting adaptation, wherein the at least one volatilization and collection equipment mounting adaptation includes a volatilization chamber mount and a collection chamber mount, mounted in the recessed work volume; and further wherein a see-through front shield is mounted to the housing and capable of being swung open in order to provide some operator access to the recessed work volume and swung closed so as to potentially shield the operator from equipment and conduct of test procedures which can be carried out in the recessed work volume, for the recessed work volume and wherein the housing includes a bottom surface.

3. The apparatus of claim 2, which includes said equipment, which equipment embraces a generally enclosed vessel capable of holding a substance for volatilization; a device for heating the substance held in the vessel; a gaseous matter entry port having an entry and exit end such that its exit end, for providing the gaseous matter to the interior of the vessel, is disposed above the boundary of the substance; an exit/collection port; and a collection device for collecting the volatilized component or components of the substance.

4. The apparatus of claim 2, wherein the recessed work volume is defined in part by two vertical walls intersecting generally normal to one another, the bottom surface intersecting generally normal to the two vertical walls defining in part the recessed work volume, and the see-through front shield which includes two generally planar, vertically oriented see-through panes intersecting generally normal to one another.

5. The apparatus of claim 2, wherein a magnetic stirring motor is present in a magnetic stirring motor containing base mounted to at least one of the two vertical walls intersecting generally normal to one another that define in part the recessed work volume.

6. The apparatus of claim 5, wherein the magnetic stirring motor containing base is upwardly-biased.

7. The apparatus of claim 2, having at least one upwardly biased base or shelf.

8. The apparatus of claim 2, wherein an operator access hole is present in a side-facing pane to the see-through front shield.

9. The apparatus of claim 3, having a clamp useful for securing a two-part volatilization vessel having a rounded glass seal, which includes a member having two generally U-shaped tines to hold the vessel together and connect it to the apparatus.

10. A lift bracket comprising a base plate containing an elongate slot; a slidable plate itself having an elongate slot, which slidable plate is attached to the base plate through a fastener that passes into and through the base plate slot and through a settable device that can pass through the slidable plate elongate slot and be attached into the base plate; a shelf; and a tensioning device which can lift the slidable plate relative the base plate.

11. The lift bracket of claim 10, wherein the tensioning device includes at least one spring spanning the base plate and the slidable plate.

12. A clamp useful for securing a two-part volatilization vessel having a rounded glass seal, which comprises a member having two generally U-shaped tines connected with a spacing block therebetween, wherein the clamp is explosively-biased, and wherein one of the tines, designated an upper tine, is connected through an upper tine support member which contains laterally disposed slots through which fasteners pass to be mounted in the upper tine thereby permitting lateral adjustment of the upper tine of the clamp.

13. The clamp of claim 12, wherein the explosively-biased feature is provided through a set of springs of the compression type mounted between the tines.

14. In a Selby-Noack test procedure, the improvement which comprises stirring at a stable, steady rate test sample liquid in a volatilization vessel.

15. The apparatus of claim 1, wherein no vacuum pump is present, but a pressure differential to said equipment is provided for by a pressurized gas.

16. The apparatus of claim 7, wherein the upwardly biased base or shelf is a lift bracket including a base plate containing an elongate slot; a slidable plate itself having an elongate slot, which slidable plate is attached to the base plate through a fastener that passes into and through the base plate slot and through a settable device that can pass through the slidable plate elongate slot and be attached into the bass plate; a shelf; and a tensioning device which can lift the slidable plate relative the base plate.

17. The apparatus of claim 16, wherein the lift bracket tensioning device includes at least one spring spanning the base plate and the slidable plate.

18. The apparatus of claim 9, wherein the two generally U-shaped tines of the clamp member are connected with a spacing block therebetween; the clamp is explosively-biased, and one of the tines, designated an upper tins, is connected through an upper tine support member which contains laterally disposed slots through which fasteners pass to be mounted in the upper tine thereby permitting lateral adjustment of the upper tine of the clamp.

19. The apparatus of claim 18, wherein the explosively-biased feature of the clamp is provided through a set of springs of the compression type mounted between the tines.

20. The apparatus of claim 1, which is useful in a Selby-Noack test procedure, which procedure includes an improvement of stirring at a stable, steady rate test sample liquid in a volatilization vessel.

* * * * *